United States Patent [19]

Bricken

[11] Patent Number: 5,003,892
[45] Date of Patent: Apr. 2, 1991

[54] PROCESS FOR STERILE DISPOSAL OF SYRINGES

[75] Inventor: Jonathan Bricken, New York, N.Y.

[73] Assignee: D.O.C.C., Inc., New York, N.Y.

[21] Appl. No.: 507,133

[22] Filed: Apr. 10, 1990

Related U.S. Application Data

[62] Division of Ser. No. 364,019, Jun. 9, 1989, abandoned.

[51] Int. Cl.⁵ .................. F23G 5/00; A61L 2/00
[52] U.S. Cl. ..................... 110/346; 423/DIG. 20; 422/1; 432/1
[58] Field of Search .............. 423/DIG. 20; 432/1, 432/2, 5, 13; 422/1; 110/346

[56] References Cited

U.S. PATENT DOCUMENTS

| | | |
|---|---|---|
| 1,222,036 | 4/1917 | Schreiber . |
| 3,360,339 | 12/1967 | Edenbaum ........................ 23/253 |
| 3,627,469 | 12/1971 | Cheng ........................... 23/232 R |
| 3,905,758 | 9/1975 | Moussou et al. ................... 432/128 |
| 4,355,227 | 10/1982 | Berard ............................. 219/390 |
| 4,376,096 | 3/1983 | Bowen ............................ 422/116 |
| 4,501,371 | 2/1985 | Smalley .......................... 215/232 |

Primary Examiner—Henry C. Yuen
Attorney, Agent, or Firm—Beth Kovitz Fields

[57] ABSTRACT

An apparatus and process for sterile disposal of used syringes is provided. The apparatus includes a heat conductive container for maintaining used syringes and a means for applying heat to the heat conductive container in an amount sufficient to melt the plastic of the syringes. The melted plastic can encapsulate the non-plastic portions of the syringe and form a molten mass. The molten mass is rendered sterile by the heat. The process for sterile disposal of used syringes in this manner is also provided.

10 Claims, 3 Drawing Sheets

PROCESS FOR STERILE DISPOSAL OF SYRINGES

This is a division of pending application Ser. No. 364,019, filed June 9, 1989, now abandoned.

FIELD OF THE INVENTION

This invention relates generally to apparatus and processes for syringe disposal and in particular, to an apparatus and process for disposal of used syringe and needle assemblies that both destroys the entire assembly and renders the destroyed assembly sterile.

BACKGROUND OF THE INVENTION

Use of syringes for injections is commonplace in hospital environments as well as in clinics and even homes for example, by diabetics and the like. As used herein, the term "syringe" broadly refers to a medical instrument used to inject fluids into the body or draw fluids from the body. In general, syringes include a plastic barrel in communication with a metal needle provided for insertion into a vein, muscle or the like. Liquid material to be injected into the body can be provided in the plastic barrel and dispensed through the needle which is in fluid communication therewith. Alternatively, body fluids can be withdrawn through the needle and collected in the plastic barrel. Because of the intimate nature of the uses to which syringes are put, it is important that they be provided initially in a sterile condition. However, syringes are no longer sterile after use. Accordingly, disposal of used syringes has become a major health problem.

There has always been and continues to be a danger that a person will stab themselves with the needle of a used syringe. This danger is heightened in this day of infectious and deadly diseases such as AIDS, hepatitis and the like since it is not possible to know if the person who used the syringe had such a disease. Consequently, all used syringes have become suspect objects of fear and are subject to strict disposal standards.

Hospitals, clinics and doctor's offices are generally required to separate the needle from the plastic barrel of the syringe and to dispose of each in separate and secure approved containers for disposal of infectious waste. In addition, infectious waste can only be removed for destruction by licensed carters, who must be hired by the hospital, clinic or doctor's office.

Numerous syringe disposal systems wherein the syringe is somehow broken or severed are known. One such system is disclosed in U.S. Pat. No. 4,565,311 issued to Pugliese et al. on Jan. 21, 1986. The device disclosed in Pugliese is a machine having knives, which are mounted so as to be capable of engaging a syringe positioned in the machine and severing the syringe in multiple locations. After severing, the parts of the syringe fall into a container and the container is disposed of as a unit.

U.S. Pat. No. 4,375,849 issued to Hanifl on Mar. 8, 1983 discloses a needle removal and disposal device including a container with a cap. The cap includes means for disengaging the needles from the syringes. The disengaged needles are stored within the container. The device does not provide means for disposing of the plastic portion of the syringe.

U.S. Pat. No. 4,452,358 issued to Simpson on June 5, 1984 shows a medical appliance disposal container having at least one opening for insertion of medical appliances. At least one of the openings includes a needle destruction means whereby needles can be destroyed while attached to a syringe and the destroyed needle-syringe assembly can be inserted into the disposal container through the opening. The disposal container is designed for use throughout a health care facility and is useful for reducing the risk of spillage if the container is upset.

U.S. Pat. No. 4,488,643 issued to Pepper on Dec. 18, 1984 discloses a disposal system for syringe and needle combinations. The system includes a container that has a lid with a flexible resilient one-way valve. The valve permits the needle and/or syringe to be inserted, but prevents reemergence of the needle and/or syringe out of the container. The lid further includes a passive bending structure which bends the needle to render it unusable prior to insertion into the container.

U.S. Pat. No. 4,553,687 issued to Harkins et al on Nov. 19, 1985 discloses yet another needle breaking and storage device. The device includes a closed compartment with an aperture in one wall for receiving a hypodermic needle and permitting it to be severed and to fall into a storage receptacle. Various ways of retaining the severed needle tips in the receptacle are disclosed including a magnet and a viscous liquid which partially coats the severed tips. The device further includes a second aperture dimensioned to similarly allow the severance of the tip of the hypodermic syringe and a separate receptacle for storage of the severed syringe tips.

A different type of syringe disposal unit is shown in U.S. Pat. No. 4,662,516 issued to Baker, Sr. et al. on May 5, 1987. The Baker apparatus includes a series of wall units, each of which include a pivoted, lockable panel and an upper opening for supporting the top surface of a thermoplastic liner contained in a basket. Medical debris is collected in the thermo-plastic liner which is periodically removed and heated in an autoclave to melt the liner around the debris. The liner is melted at a temperature of less than about 250° F. while pressure is maintained on the bag and liner. This temperature is not sufficient to melt the plastic of the syringes within the liner and accordingly, the liner and syringes are only sterile as long as the liner is not punctured. It is certainly not sufficiently sterile to meet requirements of the Federal Environmental Protection Agency (E.P.A.), the Food and Drug Administration (F.D.A.), and a significant number of Health and Sanitation Departments, namely including New York. All of the prior art syringe disposal systems are disadvantageous in that the syringe material is not rendered sterile and special disposal of the material as infectious waste is necessary.

It is, therefore, an object of the invention to provide an apparatus that processes used syringes for sterile disposal.

Another object of the invention is to provide an apparatus for processing used syringes for disposal which melts the plastic portion of the syringe so that the melted plastic can encapsulate the needle to form a melted mass and renders the melted mass sterile.

A further object of the invention is to provide a process for rendering used syringes sterile for disposal purposes.

Still other objects and advantages of the invention will in part be obvious and will in part be apparent from the specification.

SUMMARY OF THE INVENTION

Generally speaking, in accordance with the invention, an apparatus for preparing syringes for sterile disposal is provided. The apparatus includes a heat conductive container for containing at least one syringe to be prepared for disposal therein. A means for applying heat to the heat conductive container is also required. Heat is applied to the heat conductive container in an amount sufficient to melt the syringes in the container and cause the plastic portion of the syringe to encapsulate the needle of the syringe in a molten mass. The molten mass becomes sterile and does not need to be disposed of as infectious waste. The container is preferably removable from the apparatus and disposed of with the melted syringes. A process for preparing syringes for sterile disposal is also provided.

The invention accordingly comprises the several steps and the relation of one or more of such steps with respect to each of the others, and the apparatus embodying the features of construction, combination of elements and arrangement of parts which are adapted to effect such steps, all as exemplified in the following detailed disclosure, and the scope of the invention will be indicated in the claims.

DESCRIPTION OF THE DRAWINGS

For a fuller understanding of the invention, reference is had to the following description taken in connection with the accompanying drawings, in which.

DETAILED DESCRIPTION OF THE PREFERRED EMBODIMENTS

Figure 1:
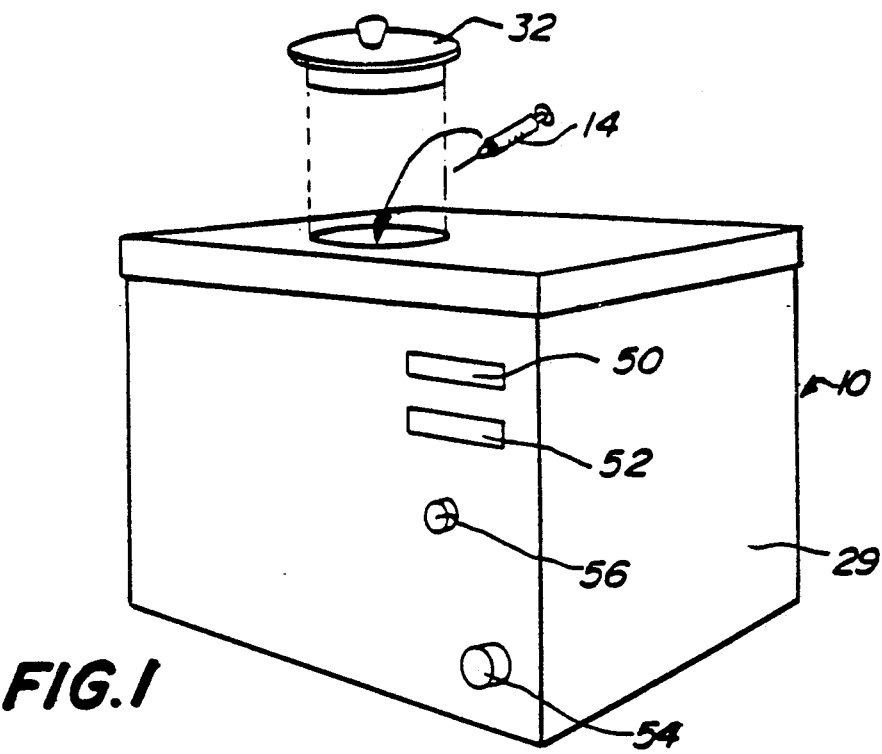
FIG. 1 is a perspective view of an apparatus for preparing syringes for sterile disposal constructed and arranged in accordance with the invention.
Figure 2:
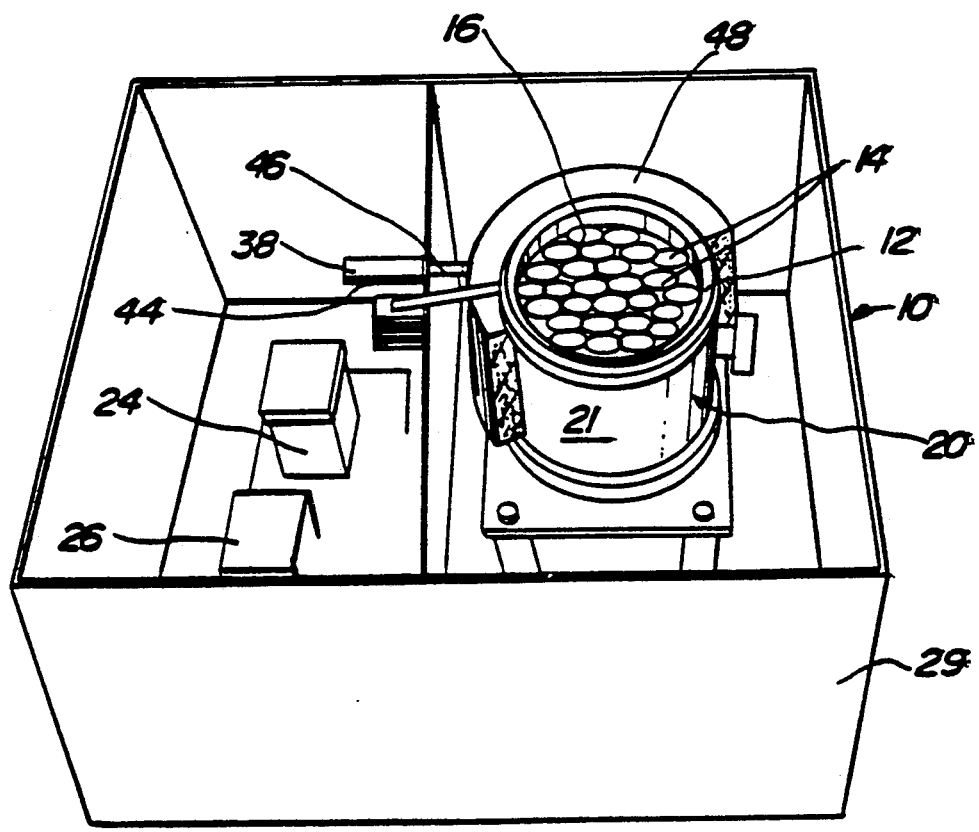
FIG. 2 is a perspective view of the interior of an apparatus for preparing syringes for sterile disposal constructed and arranged in accordance with the invention.

The syringe disposal apparatus 10 constructed and arranged in accordance with the invention includes a heat conductive container 12 and a means for applying heat to the heat conductive container 12. As shown, the means for applying heat includes an oven assembly designated generally as 20.

The heat conductive container 12 is provided for containing disposable syringes 14 which are to be prepared for sterile disposal. Heat conductive container 12 is constructed of any suitable heat conductive material such as, for example, a metal, metal alloy, glass or ceramic and certain high temperature resistant plastics. Suitable heat conductive metals include, but are not limited to, aluminum, copper and the like.

Container 12 can be any suitable size or shape for holding disposable syringes 14. While disposable syringes 14 are available in numerous different sizes and styles, container 12 may be provided for accommodating one or more predetermined styles in a particular manner or may be generally large enough to accommodate any syringe. It is generally preferable to provide a container of a size and configuration that permits the needle and plastic syringe assemblies 14 to stand with the needle pointing downward, generally in the way that pencils stand in a pencil holder. It is contemplated that the containers can be of a size and configuration that permits multiple containers to be stacked prior to use.

Container 12 has at least one opening 16 which is used to place disposable syringes 14 into container 12. A lid 18 is provided to cover opening 16. Lid 18 can be any appropriate size or shape suitable for sealing opening 16, either permanently or temporarily. The lid 18 can be of any suitable type including, but not limited to, self-sealing lids, pop-on lids, screw on lids, twist-on lids, "child" resistant or tamper-resistant lids, and the like. Furthermore, a fusable material such as a solder 19 can be provided between the container 12 and the lid 18 so that when heat is applied to the container 12 the fusable material 19 fuses the lid 18 to the container 12.

Whether the lid 18 is of a permanent or temporary type is at least partially a function of whether the entire container 12 and lid 18 having melted disposable syringes 15 therein is to be disposed of or whether the molten mass 15 of disposable syringes 14 is to be removed from container 12 prior to disposal. Obviously, if the entire container 12, lid 18 and contents 15 are to be disposed of as a unit there is no difficulty in permanently sealing lid 18 to container 12 after an appropriate number of disposable syringes 14 are placed in container 12. On the other hand, if the molten mass 15 of disposable syringes 14 is to be removed from container 12 after being subjected to heat treatment, then lid 18 must be removable from container 12 and permanent sealing is not appropriate.

In a preferred embodiment, the entire container 12 with lid 18 and contents 15 is disposed of after heat treatment. Accordingly, it is desirable for lid 18 to be permanently sealed to container 12 either prior to or during the heat treatment. Additionally, container 12 must be removable from apparatus 10 and replaceable with a new container 12. In carrying out this embodiment of the invention, it is a particularly advantageous feature if the top 17 of lid 18 and the bottom 13 of container 12 are cooperatively beveled so that used containers 12 with lids 18 secured thereto can be stacked for storage purposes. Any appropriate means for beveling lids 18 and container 12 so that multiple container 12 and lid 18 combinations can be stacked for storage is within the contemplation of the invention.

Container 12 is also preferably provided with a heat sensitive strip or indicator 40. The heat sensitive strip 40 is provided on the outside of container 12 or lid 18 so that it can be viewed when the container 12 is removed from the oven assembly 20 and is of a type that changes color at a specified predetermined temperature. The specified predetermined temperature should be the temperature that the heat conductive container 12 must achieve in order to melt the syringes 14 and is generally above 380° F. Accordingly, a user can determine at a glance whether the specified temperature has, in fact, been achieved during the heating cycle and therefore, whether the container 12 and its contents 15 can be disposed of as sterile waste.

As a separate optional feature of the lid construction of the invention, a one way opening for inserting syringes 14 into container 12 can be provided either as part of lid 18 or as separate underlid which will ultimately be covered by lid 18. Such one way openings would provide an additional safety feature. Similarly, means for snipping the needle from the syringe prior to disposing of both the needle and plastic in the container 12 might also be useful in the apparatus disclosed.

The means for applying heat to the heat conductive container may be any form of oven assembly, heating element or heater which meets the requirement of being capable of applying heat in an amount sufficient to melt the at least one syringe in the heat conductive container 12 to cause the melted plastic of the syringe 14 to encapsulate the needle as a melted mass 15 and render the melted mass 15 sterile. To accomplish these results, the means for applying heat should achieve a temperature between about 380° and 450° F. At temperatures less than about 380° F., the plastic of the syringes 14 is not melted and the plastic does not encapsulate the needle. At temperatures greater than about 450° F., neoprene rubber, which is often provided on the end of the plunger of the syringe 14, starts to burn and give off noxious fumes. Furthermore, it is not desirable to apply heat at temperatures greater than those necessary to accomplish the desired result as this results in decreased energy efficiency.

As shown in the drawings, the means for applying heat preferably includes an oven assembly designated generally as 20. Oven assembly 20 has a barrel 21 with a cover 32. The barrel 21 is of a suitable size for accommodating the heat conductive container 12 therein. A heater 30, which can be any appropriate type, provides heat to barrel 21. In turn, barrel 21 conducts heat to the heat conductive container 12 so that syringes 14 can be melted.

Oven assembly 20 also preferably includes a temperature sensor 22 mounted on a wall of the oven assembly 20. The temperature sensor 22 is a thermocouple which senses the temperature of oven assembly 20 and feeds the information to a temperature controller 24. The temperature sensor 22 also preferably includes a shut-off switch 23 which inactivates the entire system if the temerature of the oven assembly 20 climbs above a defined maximum temperature of generally about 450° F. The shut off switch 23 is normally closed and opens at about the defined maximum temperature.

The temperature controller 24 is a circuit designed to receive a signal from the temperature sensor 22. The controller 24 is preset to a desired temperature by setting the level within the controller. The signal received from the temperature sensor 22 is compared to the preset level defined by the controller 24. If the actual temperature of oven assembly 20 is either above or below the set point of the temperature controller 24, the controller 24 lowers or raises the amount of power supplied to the heater 30 until the controller 24 no longer detects a difference between the two signals. The temperature of the oven assembly 20 is accurately maintained throughout the operating cycle by this feedback process.

Oven assembly 20 also preferably includes a timer 26 so that the length of the period of time for which heat is to be applied can be regulated. The timer 26 generally includes a circuit that closes or opens switch contacts for a specified time interval in response to a signal, which is preferably an electrical signal. The timer 26 is preset to a specified time interval prior to initiation of the heat application and syringe destruction cycle and prevents oven assembly 20 from being opened during this preset time interval. In general, the preset time interval should be long enough to include the entire heat application and syringe destruction cycle as well as a cooling period during which the container 12 and oven assembly 20 have an opportunity to cool down to a temperature at which they will no longer be harmful to an operator, generally about 90° F.

Figure 4:
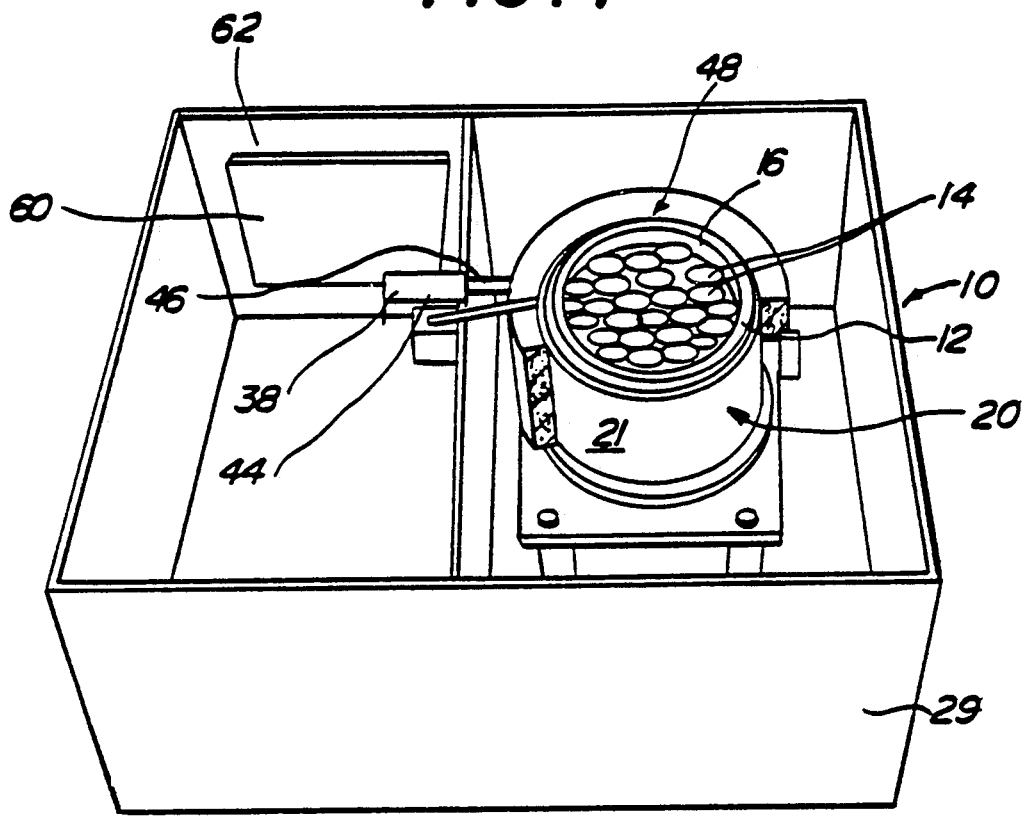
FIG. 4 is a perspective view of an alternate apparatus constructed and arranged in accordance with the invention.
Figure 5:
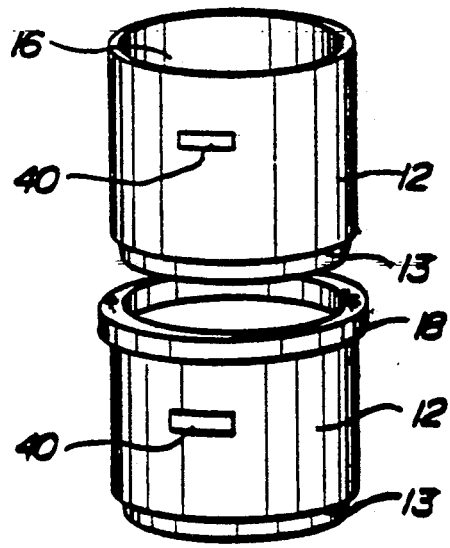
FIG. 5 is a perspective view of two heat conductive containers provided for use in the apparatus of the invention.
Figure 6:
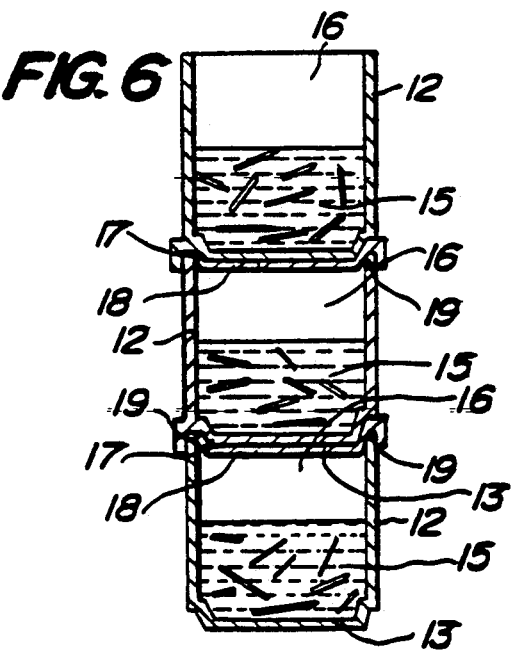
FIG. 6 is a cross-sectional view of several heat conductive containers after syringes have been prepared for sterile disposal therein.

It is further contemplated that the function of the timer 26 and the temperature controller 24 can be performed by a printed circuit board 60. Such a circuit board 60 would be positioned within housing 29 adjacent a wall 62 as shown in FIG. 4. Circuit board 60 can also then be used to control appropriate information readouts on the outside of housing 29 as discussed in more detail below.

Figure 3:
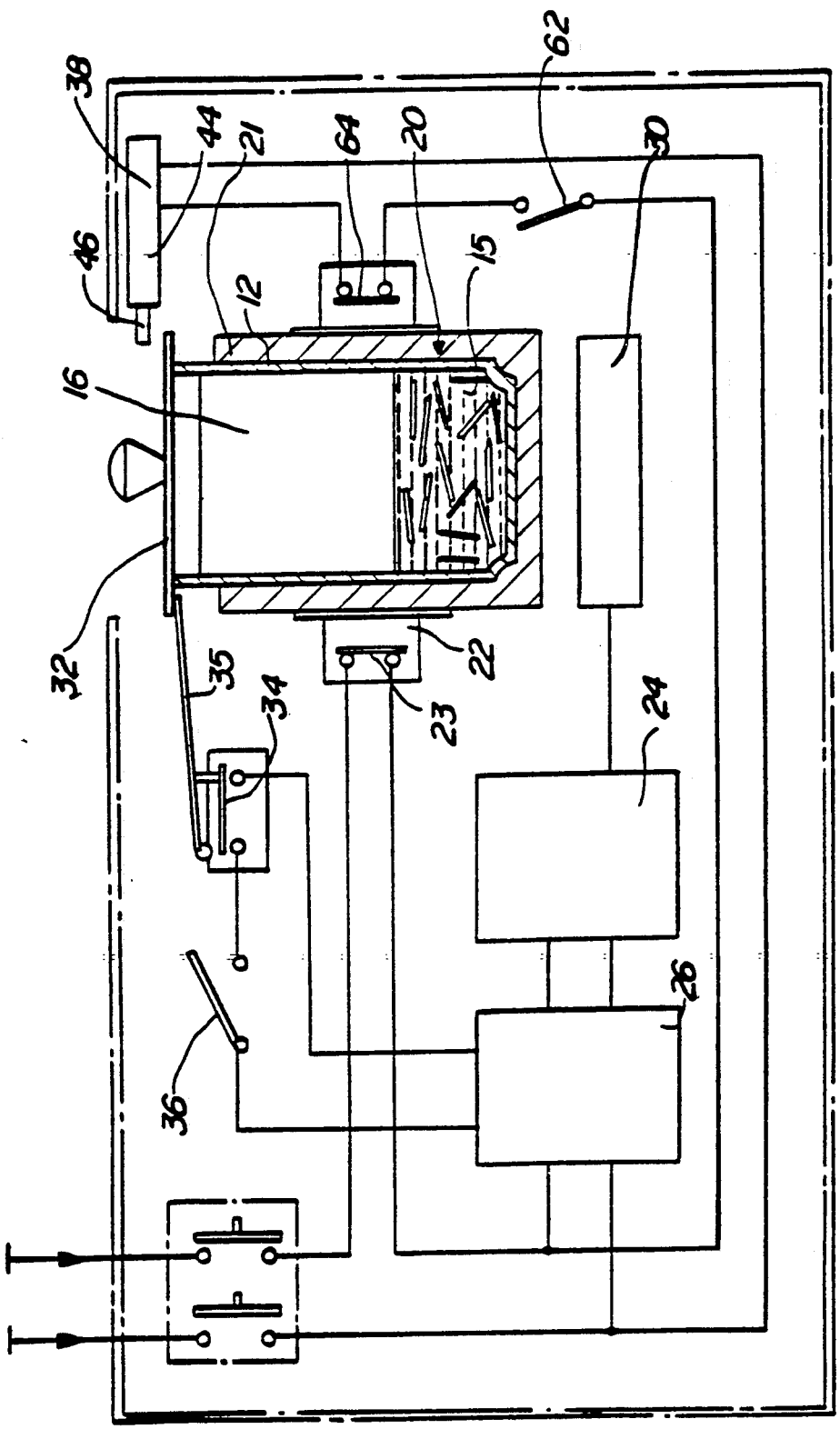
FIG. 3 is a schematic diagram showing the wiring and interlock features of an exemplary apparatus constructed and arranged in accordance with the invention.

Oven assembly 20 preferably also includes a safety interlock system of the type shown in FIG. 3. The safety interlock system is a system of electrical components within the syringe destruction apparatus 10 that protects the operator from harm. In particular, the safety interlock system prevents initiation of a heating cycle the cover 32 of oven assembly 20 is in place, prevents removal of cover 32 when the temperature of the oven assembly 20 is above a predetermined maximum safe temperature of generally about 90° F., and removes primary AC power from the entire system in the event of a temperature rise above a predetermined maximum temperature of generally about 450° F.

Cover detecting switch 34 forms part of the safety interlock system and prevents initiation of a heating cycle unless the cover 32 of oven assembly 20 is in place. Cover detecting switch 34 is preferably a normally open, lever actuated type contact switch used to detect the presence of the oven assembly cover 32. The lever 35 is spring loaded to exert force upward against the cover 32. However, pressing the cover 32 downward overcomes the spring force and causes the lever to close the switch contact when cover 32 is positioned on barrel 21 of oven assembly 20. The heating cycle cannot be initiated until cover detecting switch 34 is closed.

"On" switch 36 is also a normally open momentary contact device that is closed by the action of an operator to begin a heating cycle. "On" switch 36 must remain closed in order for the heating cycle to continue and therefore, once the heating cycle has been initiated control of "On" switch 36 is governed by timer 26.

The safety interlock system also prevents removal of the cover 32 once the heating cycle has begun and the temperature of the oven assembly 20 exceeds a predetermined maximum safe temperature, generally about 90° F. An electromagnetic solenoid 38 includes a coil of wire wrapped around a hollow cylinder. A ferrous metal rod 46 is positioned within the hollow cylinder and is spring loaded so as to be maintained within the body of the cylinder until the coil of wire is energized. When the coil is energized, a magnetic field of opposite polarity to the coil is produced in the rod 46. This causes the rod 46 to be displaced from the body of the solenoid 38. In a preferred embodiment, the rod 46 is displaced linearly for a short distance of generally about one inch. Further displacement is prevented by a retaining ring at one end of the rod 46 that contacts a cooperating ring in the interior of the hollow cylinder 44. In this energized state, the solenoid rod 46 is situated above the cover 32 and interferes with vertical movement of the cover 32.

The solenoid 38 can only be actuated for removal or insertion of the heat conductive syringe container 12 when switch 62 and thermostat contact 64 are closed. The thermostat contact 64 is always closed when the oven assembly 20 is at a temperature less than some predetermined specified temperature, generally less than about 90° F. Switch 62 is a single pole single throw contact switch that is actuated by the operator into a closed state and remains in the closed state for the time necessary to insert or remove the heat conductive container 12. The circuit is completed only when the thermostat contact 64 are closed at less than the preset predetermined temperature of generally less than about 90° F.

The thermostat contacts 23 remain closed at a predetermined maximum temperature of generally less than about 450° F. If a condition occurs that causes the temperature of oven assembly 20 to rise above that predetermined maximum temperature of generally about 450° F. the contact 23 opens and interrupt the main AC power supply to the entire system.

In a preferred embodiment, the barrel 21 of the oven assembly 20 is insulated with a suitable insulating material 48 to prevent destruction of the other elements of the system. One suitable insulating material 48 is a flexible ceramic type material having the appearance of cotton. The material may generallY have a thickness of between about ½ and ¾ inches, preferably about ½ inch.

The entire oven assembly 20 is preferably incorporated in a suitable housing or enclosure 29. Enclosure 29 is preferably constructed of stainless steel and houses the entire system in such a way as to provide insulation to the temperature controller 24, timer 26, safety interlock and other components that might otherwise be damaged by exposure to the high temperatures generated by the oven assembly 20. In addition to the layer of insulation 48 formed around oven assembly 20, enclosure 28 also preferably employs appropriate venting and/or a fan or fans to create preferential air flow away from sensitive system components.

Appropriate information readouts can be provided on the exterior of enclosure 29 for the benefit of an operator. Such readouts preferably include one or more of the temperature of the oven assembly and/or the maximum temperature to which the heating cycle has been set 50, the cycle time and/or the amount of time remaining in the cycle wherein the cycle time is defined either as the heating cycle or the heating and cooling cycle 52, an emergency shut off switch 54 and a switch for initiating operation of the apparatus, an "on" switch 56. A light or other means for indicating that the apparatus is in operation can also be used.

To use the apparatus of the invention 10, disposable syringes 14 are placed within heat conductive container 12 and lid 18 is fitted on container 12 to cover opening 16. The heat conductive container 12 is then placed within oven assembly 20 and cover 32 is secured to close cover detecting switch 34. If available, a timer 26 is set to the length of time for which the heat application cycle is to continue and the temperature setting is set to the maximum temperature which is to be achieved and maintained during the heating cycle. Switches 36 and 62 are closed by initiating the heating cycle from a switch on the exterior of enclosure 29.

Depressing the "on" switch 56 activates the heater 30 and causes the oven assembly 20 to be heated to the preset maximum temperature. A temperature sensor 22 provided on the oven assembly 20 continuously feeds a signal associated with the temperature of the oven assembly 20 to a temperature controller 24. So long as the temperature determined by the temperature sensor 22 is less than the predetermined preset temperature defined by the temperature controller 24, additional energy continues to be put into the system. When the preset predetermined temperature is reached, the temperature controller 24 maintains the oven assembly 20 at that temperature for a predetermined period of time as set by the timer 26. Solenoid 38 maintains the cover 32 of the oven assembly 20 on the barrel 21 during the heating cycle.

Should something go awry during the heating cycle, for example, if the temperature of the oven assembly 20 exceeds some predetermined maximum temperature of generally about 450° F. thermostat contact switch 23 will open, causing the supply of AC power to the entire system to be interrupted. Furthermore, an emergency shut off switch 56 provided on the exterior of the enclosure 28 can be used by an operator to shut off the entire system for any reason.

Once the system has been shut off, either due to the completion of the heating cycle as set by the timer 26, or due to an emergency-type shut off, solenoid 38 acts to retain the cover 32 on oven assembly 20 until the entire system has cooled to some predetermined maximum safe temperature of generallY about 90° F. Assuming that the system has been shut off due to completion of the heating cycle, the container 12 can be disposed of as sterile waste. Whether the container 12 has been subjected to sufficient heat to permit disposal as sterile waste can, of course, be determined by observing the color of the heat sensitive strip 40.

The disclosed apparatus and process are useful for providing safe, efficient, economical and sterile disposal of used syringes. While one presently preferred embodiment of the apparatus is discussed in detail, it will be appreciated that the invention is not limited thereto. For example, individual oven assemblies designed to melt one syringe per assembly could be provided. As another alternative, a means for applying pressure can be provided for compacting the syringes prior to, during or after the melting process.

It will thus be seen that the objects set forth above, among those made apparent from the preceding description, are efficiently attained and, since certain changes may be made in carrying out the above method and in the constructions set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A process for preparing syringes having at least a plastic portion and a needle for sterile disposal comprising:

providing a heat conductive container adapted to contain at least one syringe to be prepared for sterile disposal therein;

placing at least one syringe into the heat conductive container; and applying heat to the heat conductive container in an amount sufficient to melt the at least one syringe so that the plastic of the plastic portion can encapsulate the needle of the syringe to form a molten mass and render the molten mass sterile.

2. The process of claim 1 wherein sufficient heat is applied to raise the temperature of the heat conductive container to between 380° and 450° F.

3. The process of claim 1 wherein the heat conductive container has an opening so that the at least one syringe can be placed therein and a lid which can be positioned on the container to close the opening and wherein the process further includes placing the at least one syringe into the heat conductive container through the opening and positioning the lid on the container to close the opening.

4. The process of claim 3 wherein the container further includes means for sealing the lid to the container and wherein the process further includes sealing the lid to the container using the sealing means.

5. The process of claim 4 wherein the sealing means is a meltable material provided between the container and the lid and wherein the process further includes melting the meltable material so as to fuse the container to the lid when heat is applied to the container.

6. The process of claim 4 wherein the sealing means is solder provided between the container and the lid and wherein the process further includes soldering the container to the lid by melting the solder when heat is applied to the container.

7. The process of claim 1 wherein the container further includes a heat sensitive strip which changes color at a specified predetermined temperature provided on the outside of the container and wherein the process further includes observing a change in color of the heat sensitive strip.

8. The process of claim 1 wherein the heat conductive container is contained in an oven assembly and wherein the oven assembly includes means for maintaining the temperature of the oven assembly at a present desired temperature and means for regulating the amount of time during which heat is applied and wherein the process further includes maintaining the temperature of the oven assembly at a present desired temperature and regulating the amount of time during which the preset desired temperature is maintained.

9. The process of claim 8 wherein the means for regulating the amount of time during which heat is applied is also useful for regulating the amount of time required to cool the heat conductive container to a temperature less than about 90° C. and wherein the process further includes regulating the amount of time required to cool the heat conductive container to a temperature less than about 90° C.

10. The process of claim 1 wherein the heat conductive container is contained in a barrel of an oven assembly wherein the barrel has a cover for covering the barrel and wherein the oven assembly further includes a safety interlock system which prevents application of heat to the heat conductive container if the cover is not on the barrel of the oven assembly and wherein the process further includes placing the barrel cover on the barrel of the oven assembly so that heat can be applied to the heat conductive container.

* * * * *